United States Patent [19]
Bourque et al.

[11] Patent Number: 6,007,561
[45] Date of Patent: Dec. 28, 1999

[54] SURGICAL INSTRUMENT

[75] Inventors: Bernard J. Bourque, Tauton; Jose Lizardi, Franklin, both of Mass.

[73] Assignee: Smith & Nephew North America, Andover, Mass.

[21] Appl. No.: 09/227,181

[22] Filed: Jan. 7, 1999

Related U.S. Application Data

[62] Division of application No. 08/796,984, Feb. 7, 1997, Pat. No. 5,893,874.

[51] Int. Cl.⁶ .................................................. A61B 17/28
[52] U.S. Cl. ........................... 606/205; 606/208; 606/170
[58] Field of Search ................................... 606/205–208, 606/170, 167

[56] References Cited

U.S. PATENT DOCUMENTS

| | | | |
|---|---|---|---|
| 2,668,538 | 2/1954 | Baker et al. | 128/321 |
| 2,723,666 | 11/1955 | Greenberg | 128/321 |
| 2,790,437 | 4/1957 | Moore et al. | 128/2 |
| 3,404,677 | 10/1968 | Springer | 128/2 |
| 4,246,698 | 1/1981 | Lasner et al. | 30/134 |
| 4,271,838 | 6/1981 | Lasner et al. | 128/318 |
| 4,674,501 | 6/1987 | Greenberg | 128/305 |
| 4,712,545 | 12/1987 | Honkanen | 128/305 |
| 4,753,235 | 6/1988 | Hasson | 128/321 |
| 4,753,238 | 6/1988 | Gaiser | 128/344 |
| 4,760,848 | 8/1988 | Hasson | 128/340 |
| 4,819,633 | 4/1989 | Bauer et al. | 128/303.17 |
| 4,887,612 | 12/1989 | Esser et al. | 128/751 |
| 4,944,741 | 7/1990 | Hasson | 606/206 |
| 4,955,897 | 9/1990 | Ship | 606/210 |
| 4,977,900 | 12/1990 | Fehling et al. | 128/751 |
| 5,100,420 | 3/1992 | Green et al. | 606/143 |
| 5,133,713 | 7/1992 | Huang et al. | 606/46 |
| 5,133,735 | 7/1992 | Slater et al. | 606/205 |
| 5,133,736 | 7/1992 | Bales, Jr. et al. | 606/205 |
| 5,139,487 | 8/1992 | Baber | 604/165 |
| 5,141,519 | 8/1992 | Smith et al. | 606/205 |

(List continued on next page.)

FOREIGN PATENT DOCUMENTS

| | | |
|---|---|---|
| 0 577 423 A2 | 1/1994 | European Pat. Off. . |
| 2 346 401 | 9/1973 | Germany ........... 6/3 |
| 44 44 025 | 12/1994 | Germany ........... 17/28 |
| WO 94/20034 | 9/1994 | WIPO . |
| WO 96/32068 | 10/1996 | WIPO . |

OTHER PUBLICATIONS

Aesculap, Pro MIS Line, The complete endoscopy program from AESCULAP, Modular Instrument System.
Access Surgical International, Access By Design, Reposable Tip Scissors.
Baxter, V. Mueller Endoscopy Resposable Laparoscopic Scissors with Reuseable Tips.
Leisegang, System III, Rotating Laparoscopic Instruments.
Surgical Laparoscopy & Endoscopy, vol. 2, No. 3, 1992, Raven Press.
Microsurge, Detacha Tip, System, Multi–Use Laparoscopic Instruments, The Multi–Use Solution.
Micro Line presenting "Re–new" Tip Detachable Blade Laparoscopy Scissors.
Jarit Detach Easy 3–Step System, Directions for Detaching.
Karl Storz Endoscopy, Take–apart: a new generation of instruments, Take–apart scissors, insulated, rotating, 5 mm.
Jarit Supercut Detach Scissors, The Jarit Detach Scissors System.

(List continued on next page.)

*Primary Examiner*—Michael Buiz
*Assistant Examiner*—Kevin Truong
*Attorney, Agent, or Firm*—Fish & Richardson P.C.

[57] ABSTRACT

A medical instrument includes an elongated shaft, a plurality of implements mounted to the shaft, and an actuator coupled to produce relative movement between the implements. At least one of the implements is detachable from the shaft and the actuator and from another one of the implements. The actuator includes a distal portion with an inclined slot. One of the implements is detachably coupled to the slot such that movement of the actuator causes the relative movement between the implements. A coupler including an opening for receiving the actuator is mounted to a handle for rotation relative to the handle.

9 Claims, 10 Drawing Sheets

U.S. PATENT DOCUMENTS

| | | | |
|---|---|---|---|
| 5,147,357 | 9/1992 | Rose et al. | 606/49 |
| 5,171,258 | 12/1992 | Bales et al. | 606/205 |
| 5,192,298 | 3/1993 | Smith et al. | 606/205 |
| 5,201,752 | 4/1993 | Brown et al. | 606/190 |
| 5,201,759 | 4/1993 | Ferzli | 606/207 |
| 5,209,747 | 5/1993 | Knoepfler | 606/16 |
| 5,211,655 | 5/1993 | Hasson | 606/205 |
| 5,275,613 | 1/1994 | Haber et al. | 606/205 |
| 5,282,806 | 2/1994 | Haber et al. | 606/139 |
| 5,358,508 | 10/1994 | Cobb | 606/174 |
| 5,366,477 | 11/1994 | LeMarie, III et al. | 606/208 |
| 5,368,606 | 11/1994 | Marlow et al. | 606/170 |
| 5,391,166 | 2/1995 | Eggers | 606/48 |
| 5,421,821 | 6/1995 | Janicki et al. | 604/26 |
| 5,456,683 | 10/1995 | Fritzsch et al. | 606/41 |
| 5,470,328 | 11/1995 | Furnish et al. | 606/1 |
| 5,486,189 | 1/1996 | Mudry et al. | 606/171 |
| 5,489,290 | 2/1996 | Furnish | 606/170 |
| 5,496,317 | 3/1996 | Goble et al. | 606/48 |
| 5,498,256 | 3/1996 | Furnish | 606/1 |
| 5,507,772 | 4/1996 | Shutt | 606/205 |
| 5,632,758 | 5/1997 | Sklar | 606/170 |
| 5,868,786 | 2/1999 | DiFrancesco | 606/205 |

OTHER PUBLICATIONS

Innovative Surgical, Inc., We developed the answer to the Reusable vs. Disposable Instrument question!, Reusable or Limited use Interchangeable Tips All–In–One System–You Make the Choice.

MicroLine, Advanced Microsurgical Instrumentation, "Re–New" Disposable Tip Laparoscopic Scissors, The Benefit of Disposable with the Unique Feel of a Stainless Steel Surgical Instrument.

Microsurge, DetachaTip Laparoscopic Instruments Instructions for Use.

Apple Medical, New Scissors Help Trim Cost of Laparoscopic Surgery.

Mist, Minimally Invasive Surgical Technologies, Exciting Innovations at Your Fingertips.

Medicon Instrumente, Catalog No. 12, Surgical Instruments and Appliances.

Snowden Pencer, USA, Switch–Blades, Endoscopic Metzenbaum Scissors, The New Standard in Economical High Performance Endoscopic Scissors, Featuring Reusable Instruments and Disposable Blades.

Dimeda Instrumente GmbH.

Mist, Minimally Invasive Surgical Technologies, Our Best Ideas Come From Surgeons, Exclusive Design of Mist, Inc.

Storz, Quality Products for the Surgeon, Surgical Specialties.

American V. Mueller, The Surgical Armamentarium, Instruments Professional Equipment, Division of American Hospital Supply Corporation.

Lawton, General surgical catalogue, No. 2/80.

Miltex Surgical Instruments, Miltex Instrument Company, Inc.

Aesclap General Catalogue.

SURGICAL INSTRUMENT

This application is a divisional of U.S. application Ser. No. 08/796,984, filed Feb. 7, 1997, now U.S. Pat. No. 5,893,874.

BACKGROUND OF THE INVENTION

The invention relates to a surgical instrument, particularly to a surgical instrument for use during arthroscopic surgery.

Arthroscopic instruments generally have an actuating assembly attached to a handle with an end effector having at least one movable implement located at the distal end of the actuating assembly. Arthroscopic instruments are known which have an actuating assembly that is removable from a handle. It is also known to make arthroscopic instruments having an end effector that is replaceable as a unit.

SUMMARY OF THE INVENTION

The invention permits individual replacement of the implements of the end effector as opposed to replacement of the end effector as a unit.

In one general aspect of the invention, a medical instrument includes an elongated shaft, a plurality of implements mounted to the shaft, and an actuator coupled to produce relative movement between the implements. At least one of the implements is detachable from the shaft and the actuator and from another one of the implements.

Preferred embodiments may include one or more of the following features.

The actuator includes a distal portion with an inclined slot. One of the implements is detachably coupled to the slot such that movement of the actuator causes the relative movement between the implements. The distal portion of the actuator includes a plurality of inclined slots. Each of the implements is detachably coupled to one of the slots. The implements are scissors mounted to pivot open and closed.

The shaft includes spring arms detachably coupled to the implements. The actuator includes a proximal portion for snap-on releasable attachment of the actuator to a handle.

According to another aspect of the invention, a medical instrument includes a handle, an actuator for controlling an end effector, the actuator including a proximal portion with a tapered end section and a groove located distally of the tapered end section, and a coupler for connecting the actuator to the handle. The coupler includes an opening for receiving the actuator proximal portion and a spring loaded mechanism movable between a first position extending into the opening for engaging the groove and a second position allowing passage of the proximal portion through the opening, the tapered end acting to move the spring loaded mechanism toward the second position during insertion of the proximal portion into the opening.

Preferred embodiments of this aspect of the invention may include one or more of the following features.

A release mechanism is coupled to the spring loaded mechanism for moving the spring loaded mechanism toward the second position to allow removal of the proximal portion from the opening. The release mechanism is a spring loaded pin. The coupler is attached to the handle to rotate with respect to the handle.

According to another aspect of the invention, a medical instrument includes a handle, an actuator, a coupler for connecting the actuator to the handle, and an end effector attached to a actuator.

Preferred embodiments of this aspect of the invention may include one or more of the following features.

A shaft surrounds the actuator. The end effector includes a plurality of implements mounted to the shaft. At least one of the implements is detachable from the shaft and the actuator and from another one of the implements. The shaft includes spring arms detachably coupled to the end effector. A sheath surrounds the shaft.

According to another aspect of the invention, a detachable medical instrument includes an actuator for controlling an end effector. The actuator includes a proximal portion having a tapered end section and a groove located distally of the tapered end section for snap-on detachable coupling of the actuator to a handle. A sheath is detachably coupled to the actuator.

According to another aspect of the invention, a medical instrument includes a coupler mounted to a handle for rotation relative to the handle. The coupler includes an opening for receiving an actuator, a spring loaded mechanism movable between a first position extending into the opening for engaging the actuator and a second position allowing passage of a portion of the actuator through the opening, a release mechanism coupled to the spring loaded mechanism for moving the spring loaded mechanism toward the second position to allow removal of the portion from the opening, and a positioning member which interfaces with the handle to position the coupler in a desired rotated position relative to the handle.

According to another aspect of the invention, an end effector for a medical instrument of the kind that includes an actuating member for actuating the end effector has a pair of implements configured for releasable connection to each other and to the actuating member.

Preferred embodiments of this aspect of the invention may include one or more of the following features.

Each of the pair of implements includes a working portion, a coupler in the form of a coupling pin which is received in a corresponding slot in the actuating member, and a coupler configured for releasably connecting the pair of implements to each other.

The medical instruments of the invention may be used in arthroscopic procedures in which, for example, scissors or graspers are employed. The medical instruments can be adapted to connect to a power source for use in procedures where cauterization capability is desired.

Advantages of the invention include detachable implements which permit individual replacement of dulled blades without the need for any further components to be disposable, thus providing a cost effective disposable system. Additionally, instruments according the invention can be quickly disassembled such that components can be individually cleaned and easily reassembled.

Other features and advantages of the invention will be apparent from the following detailed description, and from the claims.

DESCRIPTION OF THE PREFERRED EMBODIMENTS

Figure 1:
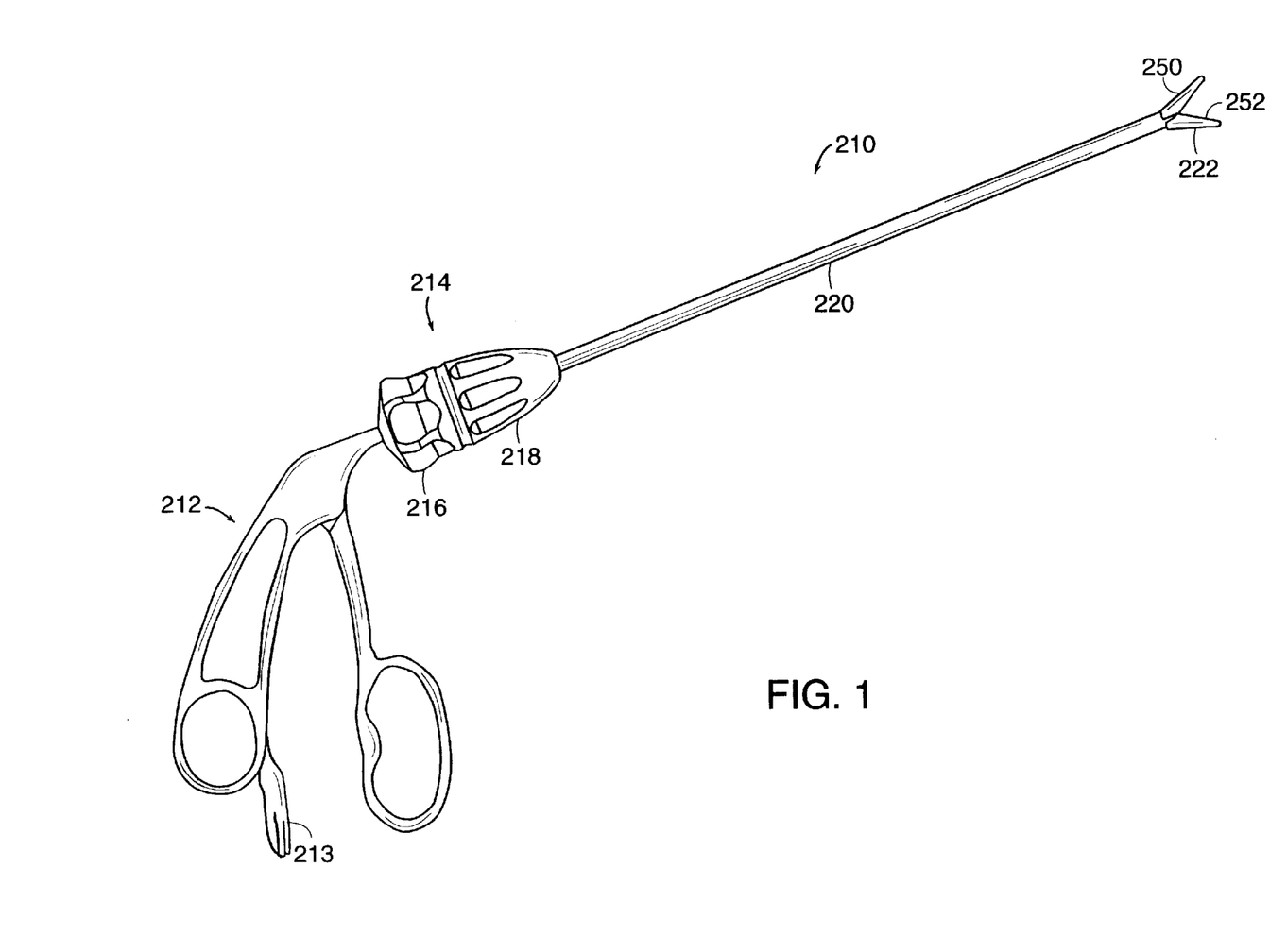
FIG. 1 is a diagrammatic illustration of a medical instrument.

Referring to FIG. 1, an arthroscopic instrument 210 includes a handle 212, a coupler 214 with base section 216 and cover 218, and a tube assembly 220 with a detachable end effector 222, e.g., a scissor dissector. Handle 212 has an electrical connector 213 which attaches to a power source (not shown) to permit cauterization of tissue with end effector 222.

End effector 222 includes implements 250, 252, e.g., cutting blades, which become dulled with use. In order to replace one or both dulled implements, implements 250, 252 are individually detachable from each other and from tube assembly 220.

Figure 2:
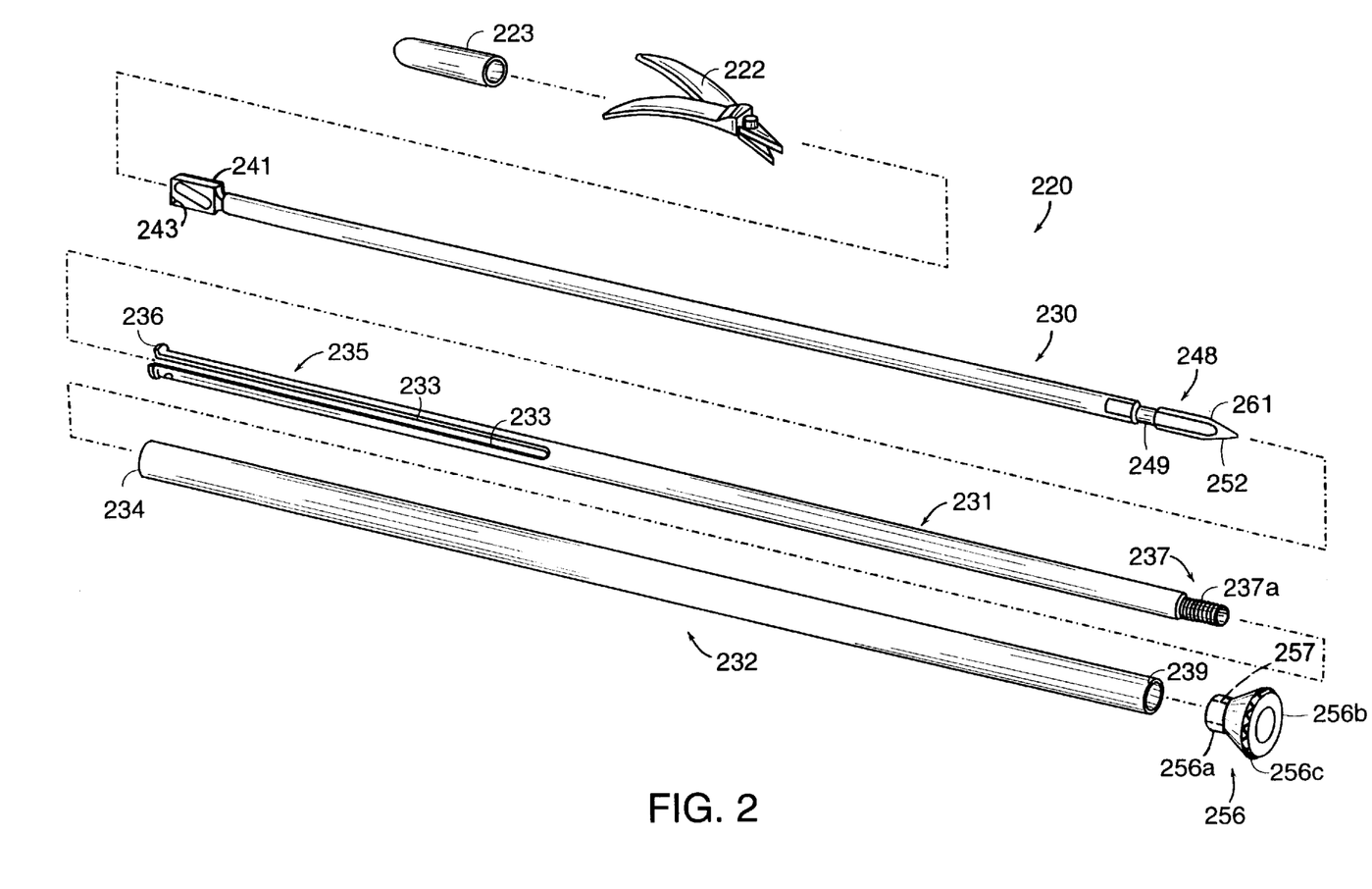
FIG. 2 is an exploded view of the medical instrument of FIG. 1.

Referring to FIG. 2, end effector 222 is detachably coupled to an actuator 230 and an intermediate shaft 231 of tube assembly 220. Actuator 230 terminates in a distal coupler 241, and shaft 231 terminates in a distal coupling section 235 with spring arms 233, described further below, for detachably coupling end effector 222 to actuator 230 and shaft 231.

An outer sheath 232 of tube assembly 220 is hollow to accommodate the insertion of shaft 231 into sheath 232, and shaft 231 is hollow to accommodate the insertion of actuator 230 into shaft 231. Shaft 231 includes a proximal section 237 with external threads 237a which extend beyond a proximal end 239 of sheath 232 when tube assembly 220 is assembled. A spacer 256 has a distal section 256a with internal threads 257 for threaded engagement with proximal threads 237a of shaft 231 and a proximal, enlarged section 256b. Section 256b has a knurled edge 256c to aid in threading spacer 256 onto shaft 231. Alternatively, instead of spacer 256 being a separate component, spacer 256 can be integral with sheath 232. When instrument 210 is assembled spacer 256 is positioned between base section 216 and cover 218 to prevent axial movement of shaft 231 and sheath 232 when actuator 230 is moved axially.

A distal end 236 of shaft coupling section 235 has an increased outer diameter against which a distal end 234 of sheath 232 abuts when assembled. With tube assembly 220 assembled, a proximal end 248 of actuator 230 extends outside proximal section 237 of shaft 231. Proximal end 248 of actuator 230 includes a tapered portion 252, a groove 249, and a flattened section 261 (there being a corresponding flattened section, not shown, on the opposite side of proximal end 248) for coupling actuator 230 to coupler base section 216, described further below. Groove 249 has a width, e.g., of about 0.045", a diameter, e.g., of about 0.065", and actuator 230 has a diameter, e.g., of about 0.095".

Figure 3:
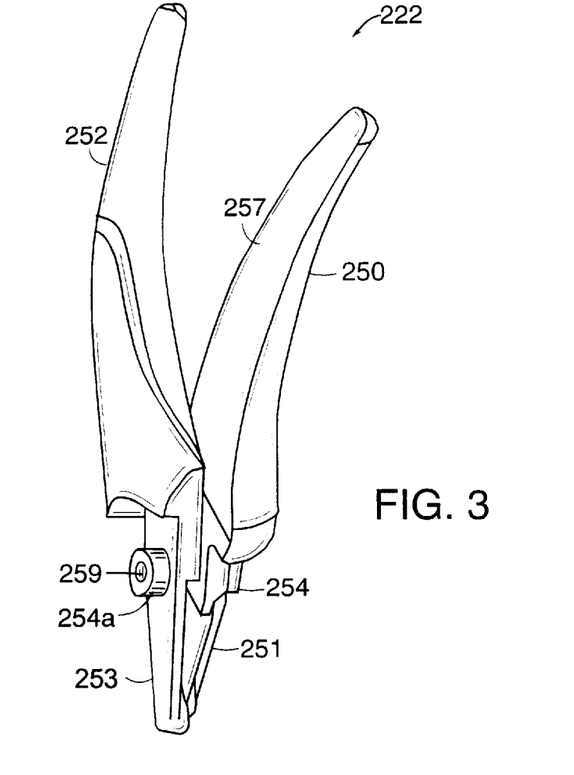
FIGS. 3 and 3A are diagrammatic illustrations of an end effector of the medical instrument of FIG. 1.
Figure 3A:
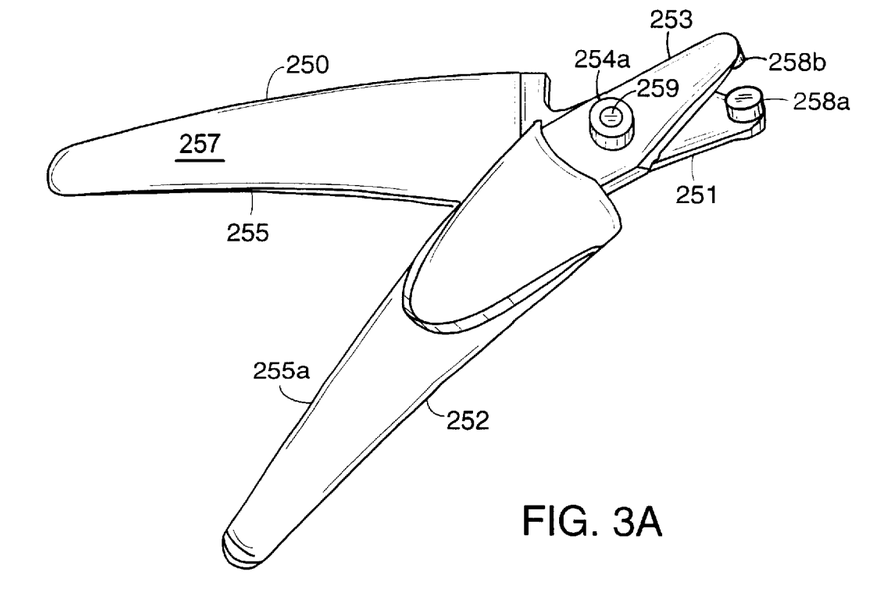

Referring to FIGS. 3 and 3A, implements 250, 252 of end effector 222 include coupling members 251, 253, respectively, having shaft couplers 254, 254a, respectively, through which a pin 259 passes to attach implements 250, 252 to each other. Pin 259 can be integral with one of the implements 250, 252, or not. Implements 250, 252 rotate with respect to each other about pin 259 to open and close. Implements 250, 252 includes cutting edges 255, 255a, respectively, and are arched with surface 257 of implement 250 contacting a corresponding surface (not shown) of implements 252.

Figures 4, 4A:
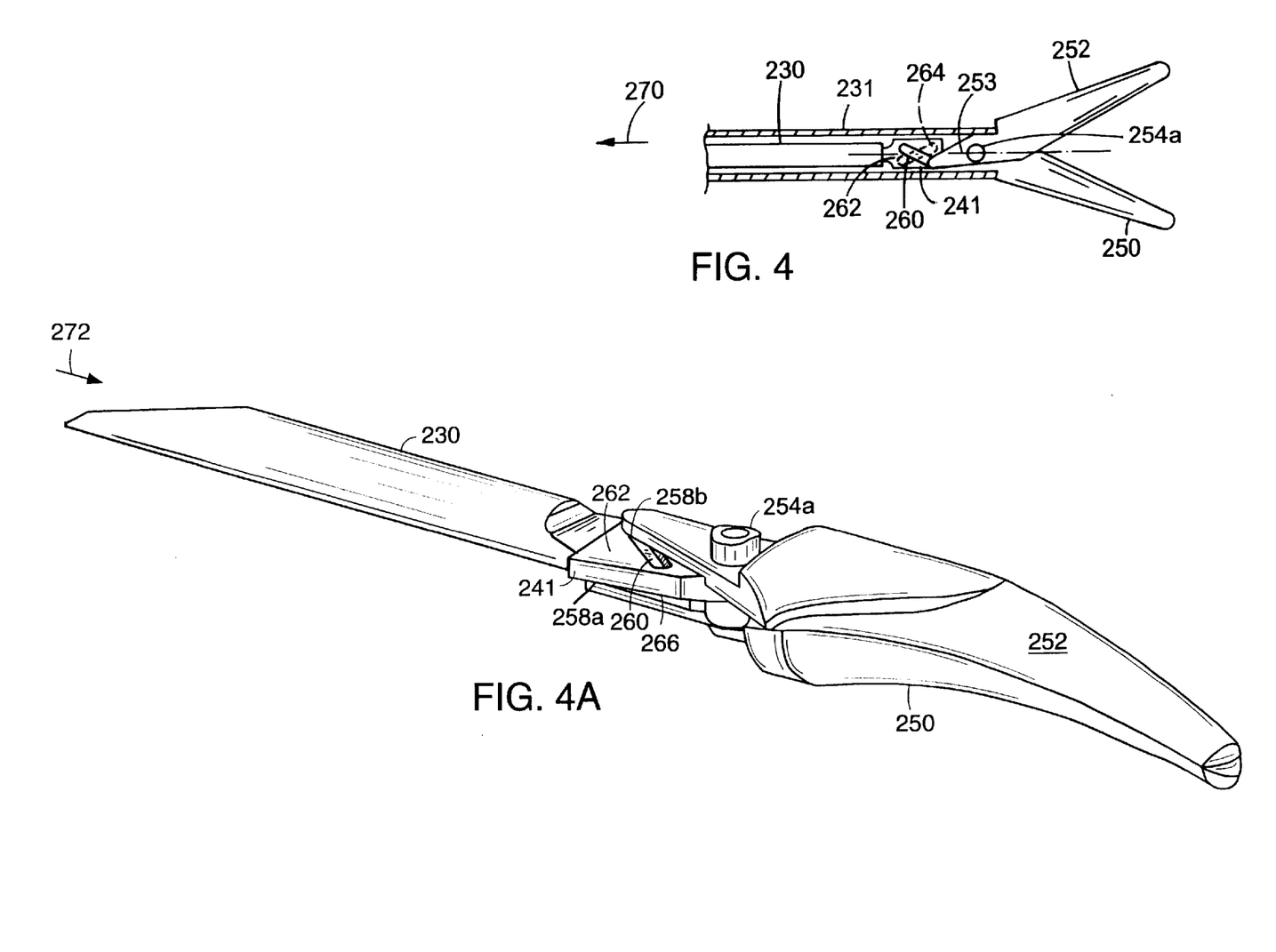
FIG. 4 is a cross-sectional view of the distal end of the medical instrument of FIG. 1, shown with an outer tube removed.
FIG. 4A is a diagrammatic illustration of the distal end the medical instrument of FIG. 1, showing an actuator coupled to an end effector.

Referring to FIGS. 4 and 4A, distal coupler 241 of actuator 230 includes a slot 260 on one face 262 of distal coupler 241 and a second slot 264 located on the opposite face 266 of distal coupler 241. As seen in FIG. 4, slots 260, 264 are inclined to form an "X". An actuator coupling pin 258a (FIG. 3A) of implement 250 is positioned in slot 264 and an actuator coupling pin 258b of implement 252 is positioned in slot 260.

Figure 5:
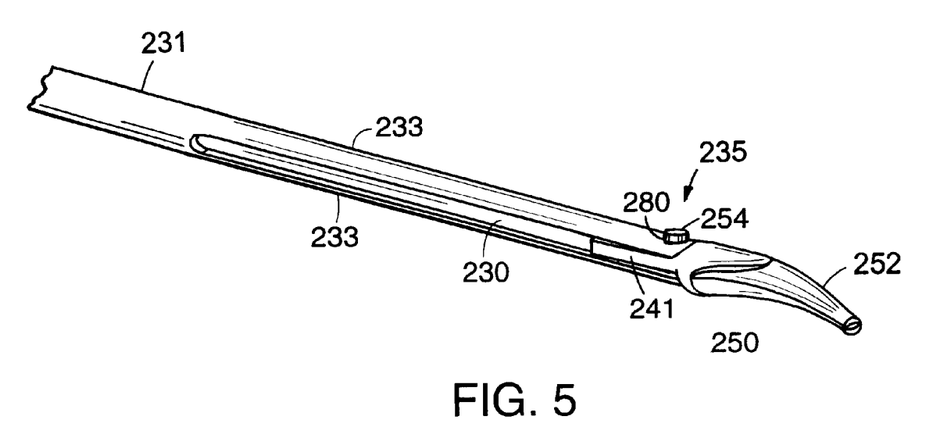
FIG. 5 is a diagrammatic illustration of the distal end of the medical instrument of FIG. 1, shown with an outer tube removed.

Referring to FIG. 5, spring arms 233 each include a hole 280, only one hole being shown, for receiving a respective coupler 254 of implements 250, 252 to attach the implements to shaft 231.

With shaft 231 holding implements 250, 252 axially stationary during axial, proximal motion of actuator 230 (arrow 270, FIG. 4), actuator coupling pins 258a, 258b slide within slots 264, 260, respectively, while slots 260, 264 move proximally. Due to the inclination of slots 260, 264 relative to the axial direction, moving actuator 230 proximally causes implements 250, 252 to open. During distal motion of actuator 230 (arrow 272, FIG. 4A), actuator coupling pins 258a, 258b slide within slots 260, 264 while slots 260, 264 move distally. Moving actuator 30 distally causes implements 250, 252 to close.

Spring arms 233 are outwardly flexible to permit insertion of end effector 222 into shaft 231. A cap 223 (FIG. 2) can be used to help hold implements 250, 252 together during assembly.

To assemble tube assembly 220, actuator 230 is first placed within shaft 231 with distal coupler 241 extending out of distal end 236 of shaft 231. Actuator coupling pins 258a and 258b of implements 250, 252 are placed in slots 264, 260, respectively. To aid in the placement of coupling pins into slots 264, 260, each pins 258a, 258b is initially positioned in a detent 243 located on distal coupler 241 (see FIG. 2, a corresponding detent, not shown, being located on the opposite side of distal coupler 241). Detents 243 are aligned with slots 264, 260 such that after placement of pins 258a, 258b in detents 243, pushing implements 250, 252 proximally locates pins 258a, 258b in the proximal ends of slots 264, 260.

Actuator 230 is then pulled proximally such that distal coupler 241 is located within shaft 231. Arms 233 of shaft 231 are flexed outward to enable couplers 254, 254a to be aligned with holes 280 in shaft 231. Arms 233 are then released resulting in couplers 254, 254a being located in holes 280. Outer sheath 232 is then slid over shaft 231 and adapter 256 is threaded onto proximal section 237 of shaft 231.

To remove implements 250, 252 from actuator 230 and shaft 231, outer sheath 232 and adapter 256 are removed from shaft 231 and actuator 230 surrounded by shaft 231 is connected to coupler 214, described further below. By holding shaft 231 while rotating coupler 214 (which causes rotation of actuator 230) arms 233 of shaft 231 are flexed outward by distal coupler 241 of actuator 230 causing implements 250, 252 to be released from holes 280 in shaft 231 and removed from actuator 230. The releasable coupling of implements 250, 252 to each other and to actuator 230 and shaft 231 enables one or both implements 250, 252 to be replaced when worn.

Figures 6, 6A:
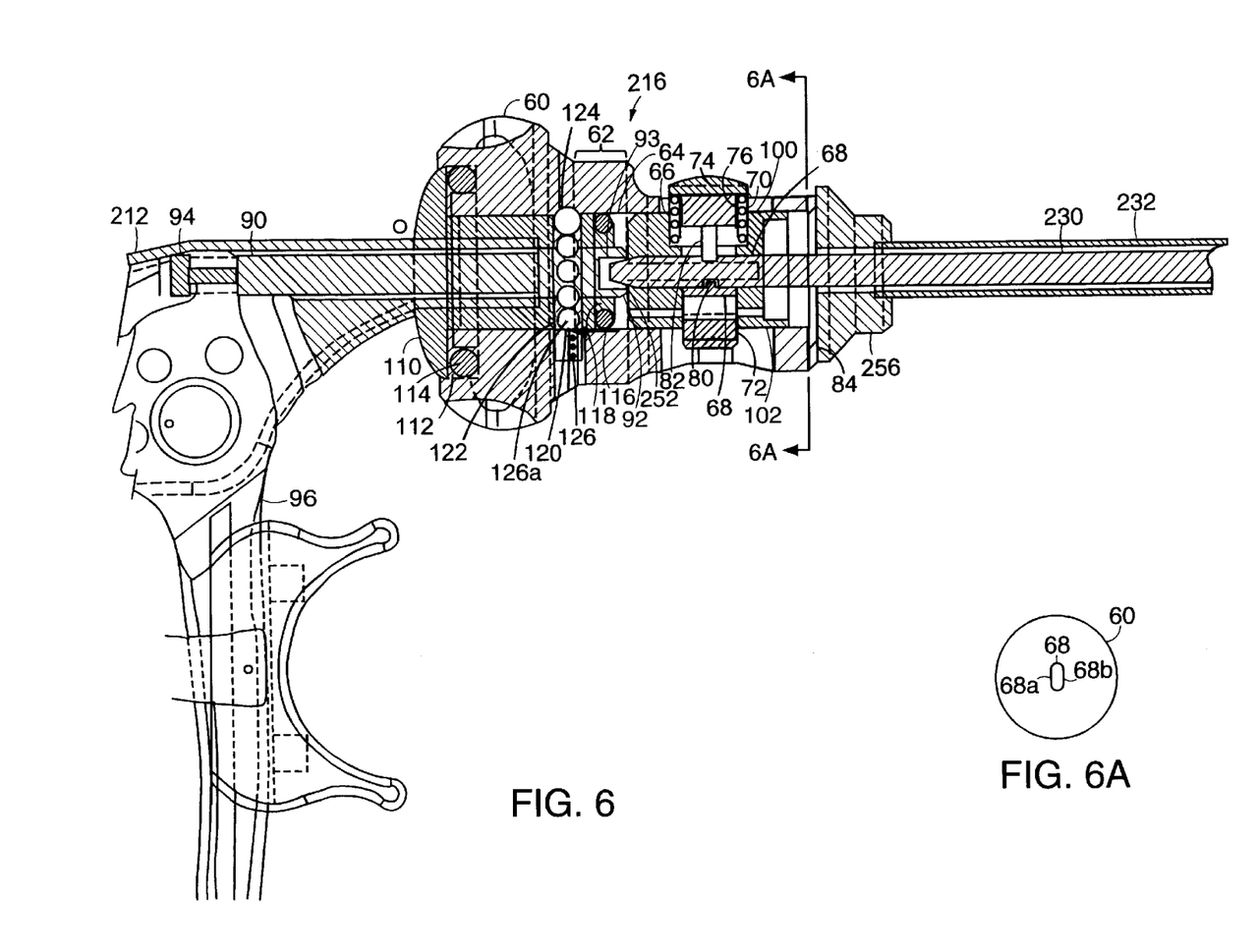
FIG. 6 is a cross-sectional view of a coupler of the medical instrument of FIG. 1, shown with a cover removed.
FIG. 6A is an end view of the coupler, taken along lines 6A—6A in FIG. 6.

Referring to FIG. 6, in which coupler 214 is shown with cover 218 removed, the base section 216 of coupler 214 includes a housing 60 with a through channel 64. A coupling member 66 located in channel 64 has a through bore 68 for receiving proximal end 248 of actuator 230. Channels 70, 72 in coupling member 66 intersect bore 68 and house a pin 74 and spring 76 for loading pin 74. A hole 82 in pin 74 permits passage of actuator 230 through pin 74. Spring 76 biases pin 74 upwardly, as viewed in FIG. 6, such that a wall 80 of hole 82 extends into bore 68 of coupling member 66.

Tapered portion 252 on proximal end 248 helps to guide actuator 230 into bore 68 during insertion of actuator 230 into coupler 214 and acts to push pin 74 downwardly against the force of spring 72 to move wall 80 out of through bore 68. When groove 249 of actuator 230 is aligned with wall 80, pin 74 moves upward due to the force of spring 76, and wall 80 moves into position in groove 249 to lock actuator 230 to base section 216. To remove actuator 230 from coupling member 66, pin 74 is manually depressed against the force of spring 76 to disengage wall 80 from groove 249.

Referring to FIG. 6A, bore 68 has flattened sides 68a, 68b. Actuator 230 is placed in bore 68 with flats 261 aligned with bore flats 68a, 68b. Actuator 230 is thus keyed to bore 68 such that rotation of coupler 214 also causes rotation of actuator 230.

Referring again to FIG. 6, housing 60 includes an externally threaded section 62 for attachment of internal threaded cover 218 over housing 60. With actuator 230 locked into position in housing 60, spacer 256 abuts a distal surface 84 of housing 60. Cover 218 captures spacer 256 against surface 84 when threaded onto housing 60 to prevent axial movement of spacer 256, and thus shaft 231 and sheath 232, during axial movement of actuator 230.

Handle 212 is coupled to actuator 230 and member 66 by a trigger rod 90. A distal end 92 of trigger rod 90 abuts coupling member 66 and includes a distal cut out 93 for receiving actuator 230. A proximal end 94 of trigger rod 90 is coupled to a pivotable trigger 96 of handle 212. Actuation of trigger 96 causes axial movement of trigger rod 90 and thus axial motion of coupling member 66 and actuator 230. Slots 100, 102 in housing 60 provide clearance for movement of pin 74 with coupling member 66.

Handle 212 includes an integral mount 110 for rotatably mounting housing 60 to handle 212. A circumferential groove 112 in housing 60 contains an o-ring 114 providing a seal between housing 60 and mount 110. A second o-ring 116 located in a second circumferential groove 118 in mount 110 also provides a seal between housing 60 and mount 110. A third circumferential groove 120 in mount 110 includes surface detentes 122 spaced around the circumference of groove 120. A dowel pin 124 and a ball plunger 126 extend through housing 60 to groove 120. Dowel pin 124 is press fit into place to couple mount 110 to housing 60 while permitting rotation of housing 60 relative to mount 110. Ball 126a of ball plunger 126 is spring biased to enter detentes 122 as housing 60 is rotated to aid in rotationally positioning housing 60, and thus end effector 222.

In use, cover 218 is placed onto sheath 232 and actuator 230, shaft 231 and end effector 222 are assembled and positioned within sheath 232 to form tube assembly 220 (FIG. 2). Tube assembly 220 is then coupled to base section 216 of coupler 214 by "snapping" proximal end 248 of actuator 230 into place, and cover 218 is threaded onto base section 216 to capture spacer 248.

Instrument 210 can be easily disassembled for cleaning. Tube assembly 220 can be easily removed from base section 216 by removing cover 218, depressing pin 74, and removing proximal end 248 of actuator 230 from base section 216. Tube assembly 220 can then be disassembled to permit cleaning of actuator 230, shaft 231, sheath 232, and end effector 222, and to permit replacement of one or both implements 250, 252.

The coupling mechanism for joining actuator 230 to coupler 214, described above, provides a simple method of attaching and detaching tube assembly 220 and coupler 214. Coupler 214 is not limited to use with tube assembly 220 and can be used with any medical instrument having an actuator with a proximal end 248 for "snap-on" joining to coupler 214.

Figure 7:
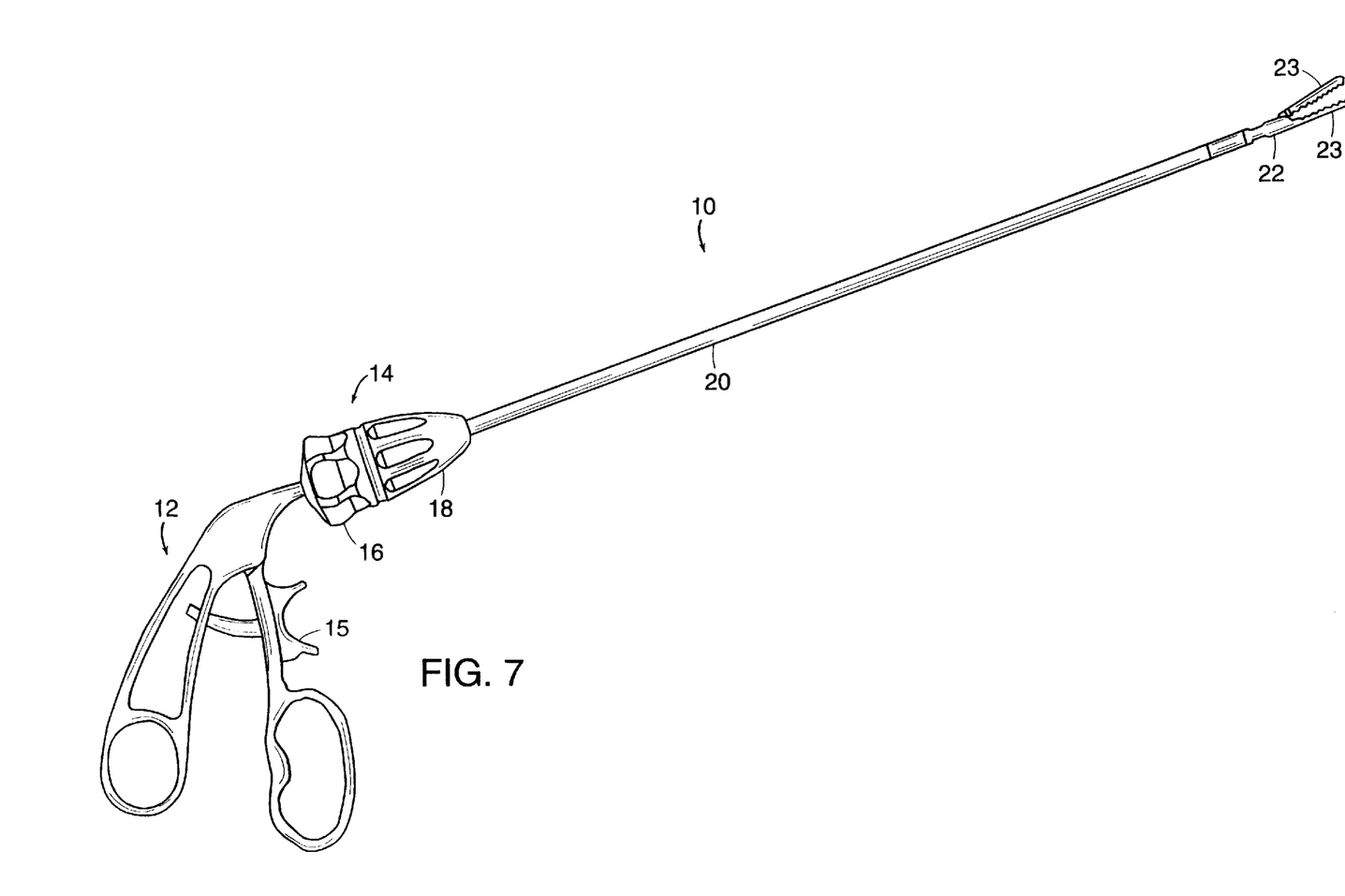
FIG. 7 is a diagrammatic illustration of an additional embodiment of a medical instrument.

Referring to FIG. 7, an arthroscopic instrument 10 includes a handle 12, a handle lock 15, a coupler 14 with a base section 16 and a cover 18, identical to coupler 214 described above, and a tube assembly 20 with a distal end effector 22, e.g., a grasper or dissector. End effector 22 may include one or more moveable members 23. Tube assembly 20 is removable from coupler 14 and can be disassembled, described below, to facilitate cleaning of instrument 10.

Figure 8:
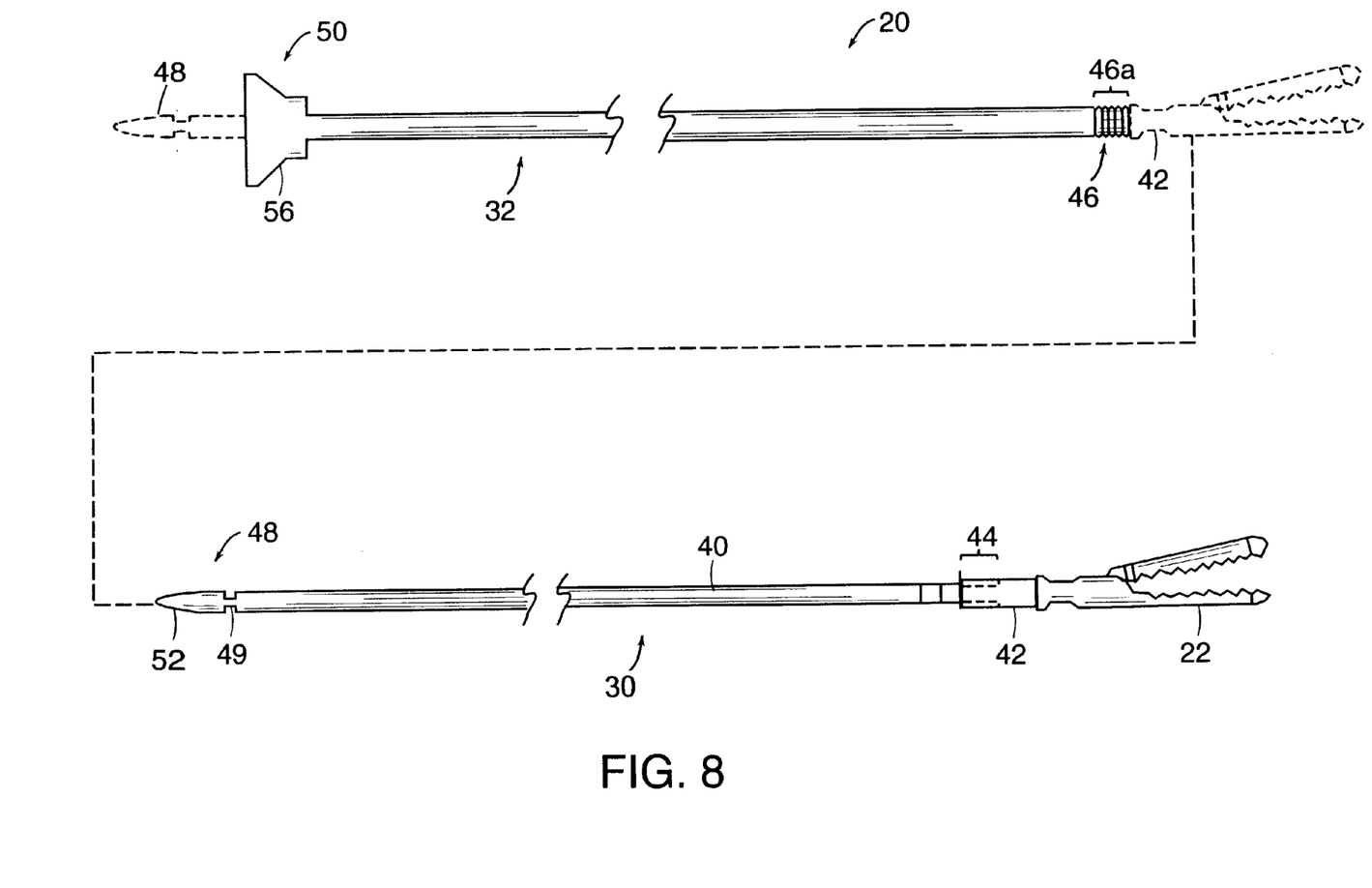
FIG. 8 is an exploded view of the medical instrument of FIG. 7.

Referring to FIG. 8, tube assembly 20 includes an actuator 30 terminating in distal end effector 22, and a hollow outer sheath 32 through which actuator 30 is placed (shown in phantom). Actuator 30 includes a rod 40 and a distal tube 42 radially spaced from rod 40 which are both coupled to end effector 22 as described, e.g., in U.S. Pat. No. 4,712,545 to Honkanen. Tube 42 has an internally threaded section 44. Sheath 32 has a proximal section 46 with external threads 46a for attaching actuator 30 to sheath 32 by insertion of section 46 into tube 42 (shown in phantom) and threaded engagement of sections 44 and 46. In an alternative, preferred embodiment, tube 42 is externally threaded at section 44 and sheath 32 is internally threaded at proximal section 46.

With actuator 30 positioned inside and threadedly attached to sheath 32, a proximal end 48 of actuator 30 extends outside a proximal end 50 of sheath 32 (shown in phantom). Proximal end 48 of actuator 30 includes a tapered portion 52 and a groove 49 for coupling actuator 30 to coupler base section 16, as described above. Proximal end 50 of sheath 32 includes a spacer 56 which, when instrument 10 is assembled, is captured between base section 16 and cover 18 to prevent axial movement of sheath 32, and thus tube 42, when actuator 30 is moved axially.

In use, cover 18 is placed onto sheath 32 and actuator 30 is positioned within sheath 32 to form tube assembly 20. The tube assembly 20 is then coupled to base section 16 of coupler 14 by "snapping" proximal end 48 of actuator 30 into base section 16, and cover 18 is threaded onto base section 16.

Tube assembly 20 can be easily removed from base section 16 by removing cover 18, depressing pin 74, and removing proximal end 48 of actuator 30 from base section 16. Tube assembly 20 can then be disassembled by unscrewing sheath 32 from actuator 30 to permit cleaning of actuator 30, sheath 32, and end effector 22.

End effector 22 can be coupled to tube assembly 20 in the manner described above with reference to FIGS. 4–5.

Other embodiments are within the scope of the following claims.

Figure 9:
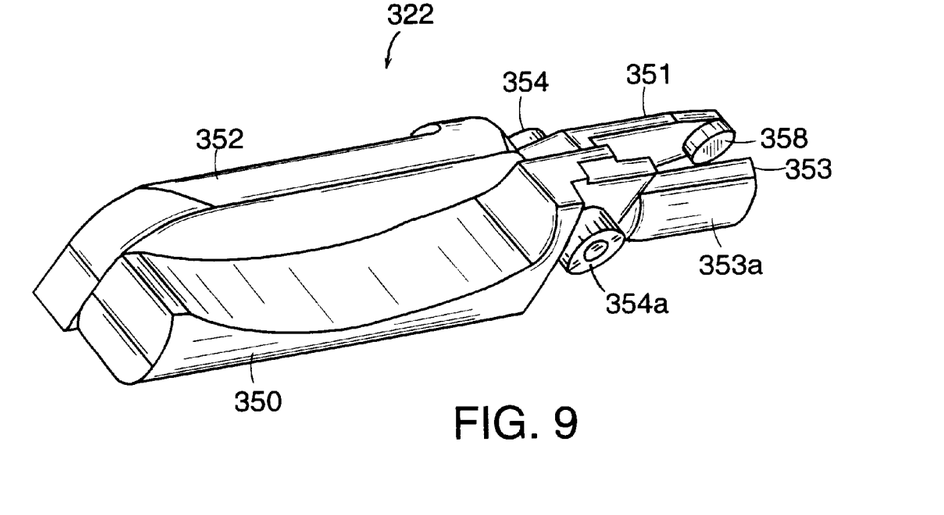
FIGS. 9 and 9A are diagrammatic illustrations of an alternative embodiment of an end effector of the medical instrument of FIG. 1.
Figure 9A:
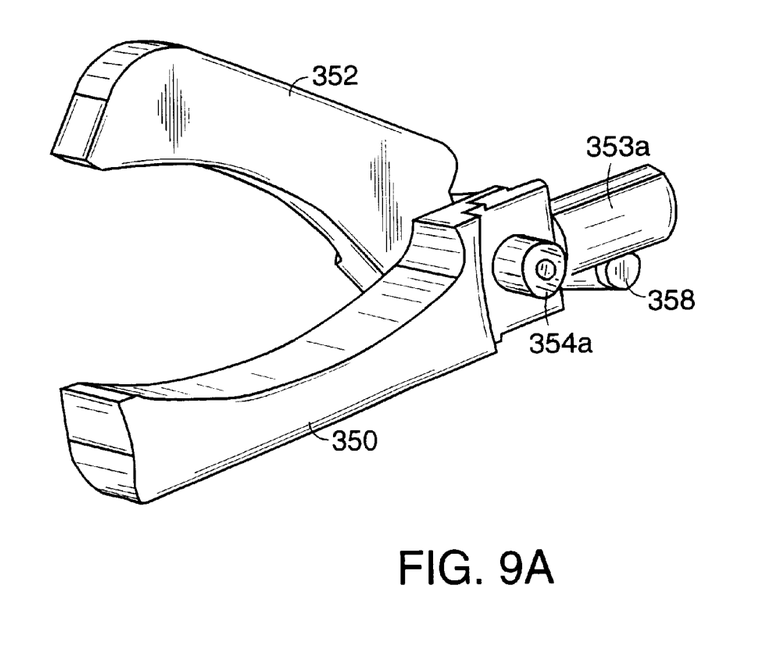

For example, referring to FIGS. 9 and 9A, actuator distal coupler 241 can be used with an end effector 322, e.g., a grasper or cutter, having a fixed implement 350 and a movable implement 352. Implements 350, 352 include coupling members 351, 353, respectively, having shaft couplers 354, 354*a*. Coupling member 351 of movable implement 352 includes an actuator coupling pin 358 which is positioned in slot 264 of coupler 241 such that movement of actuator 230 causes implement 252 to open and close as described above. Coupling member 353 of fixed implement 350 does not include an actuator coupling pin and has a contoured outer surface 353*a* having a radius corresponding to the inner radius of shaft 231. Fixed implement 350 is therefore not coupled to actuator 230 and contoured surface 353*a* insures that implement 350 remains stationary during axial movement of actuator 230 to open and close movable implement 352.

Figure 10:
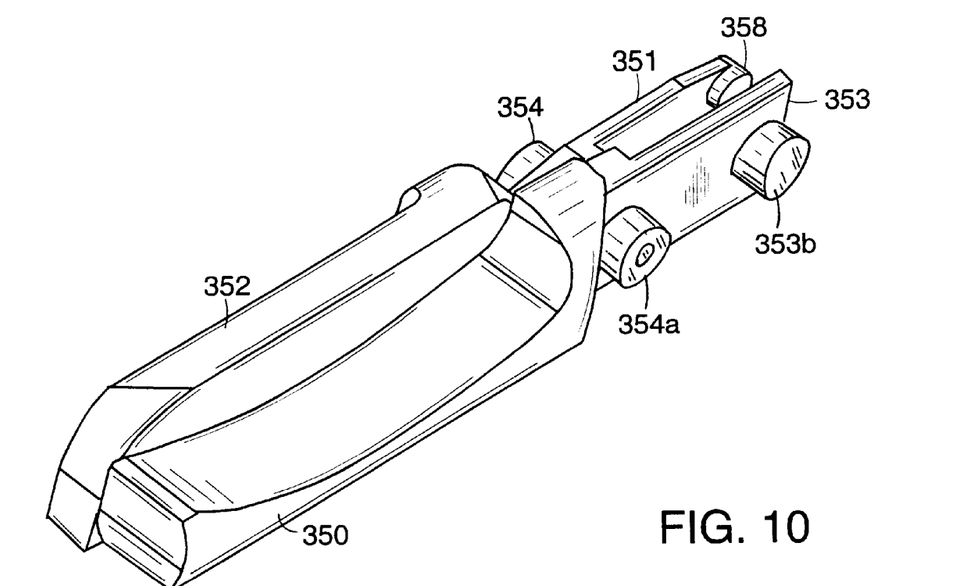
FIGS. 10 and 10A are diagrammatic illustrations of an additional alternative embodiment of an end effector of the medical instrument of FIG. 1.
Figure 10A:
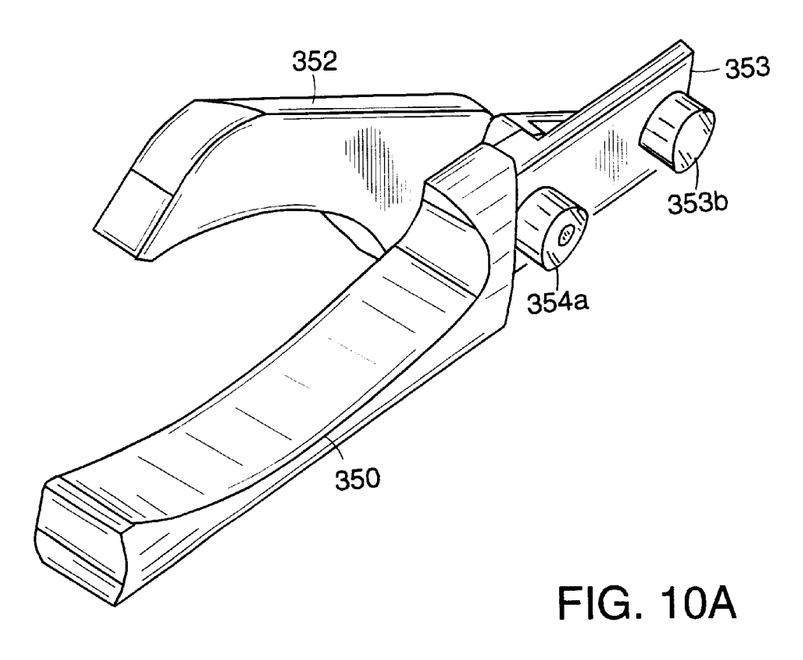

Referring to FIGS. 10 and 10A, alternatively, coupling member 353 of fixed implement 350 has a fixation knob 353*b* which abuts shaft 231 to insure that implement 350 remains stationary during axial movement of actuator 230 to open and close movable implement 352.

What is claimed is:

1. A medical instrument, comprising:

a handle, an actuator for controlling an end effector, said actuator including a proximal portion with a tapered end section and a groove located distally of said tapered end section, and a coupler for connecting said actuator to said handle, said coupler including an opening for receiving said actuator proximal portion and a spring loaded mechanism movable between a first position extending into said opening for engaging said groove and a second position allowing passage of said proximal portion through said opening, said tapered end acting to move said spring loaded mechanism toward said second position during insertion of said is proximal portion into said opening.

2. The medical instrument of claim 1 further comprising a release mechanism coupled to said spring loaded mechanism for moving said spring loaded mechanism toward said second position to allow removal of said proximal portion from said opening.

3. The medical instrument of claim 2 wherein said release mechanism comprises a spring loaded pin.

4. The medical instrument of claim 1 wherein said coupler is attached to said handle to rotate with respect to said handle.

5. A medical instrument, comprising:

a handle, an actuator including a proximal portion with a tapered end section and a groove located distally of said tapered end section, a coupler for connecting said actuator to said handle, said coupler including an opening for receiving said actuator proximal portion and a spring loaded mechanism movable between a first position extending into said opening for engaging said groove and a second position allowing passage of said proximal portion through said opening, said tapered end acting to move said spring loaded mechanism toward said second position during insertion of said proximal portion into said opening, and an end effector attached to said actuator.

6. The medical instrument of claim 5 further comprising a shaft surrounding said actuator.

7. The medical instrument of claim 6 wherein said end effector includes a plurality of implements mounted to said shaft, at least one of said implements being detachable from said shaft and said actuator and from another one of said implements.

8. The medical instrument of claim 6 wherein said shaft includes spring arms detachably coupled to said end effector.

9. The medical instrument of claim 6 further comprising a sheath surrounding said shaft.

* * * * *

UNITED STATES PATENT AND TRADEMARK OFFICE
CERTIFICATE OF CORRECTION

| | | |
|---|---|---|
| PATENT NO. | : 6,007,561 | Page 1 of 1 |
| DATED | : December 28, 1999 | |
| INVENTOR(S) | : B. J. Bourque et al. | |

It is certified that error appears in the above-identified patent and that said Letters Patent is hereby corrected as shown below:

<u>Title page,</u>
Item [73], Assignee: please delete "Smith & Nephew North America. Andover, Mass." and replace with -- Smith & Nephew, Inc., Memphis, Tenn. --

Signed and Sealed this

Eighth Day of October, 2002

Attest:

Attesting Officer

JAMES E. ROGAN
*Director of the United States Patent and Trademark Office*